United States Patent [19]
Smith et al.

[11] 4,132,900

[45] Jan. 2, 1979

[54] OPTICAL POINTER FOR RADIOGRAPHIC APPARATUS

[75] Inventors: William E. Smith, Fremont; Robert J. Rorden, Los Altos, both of Calif.

[73] Assignee: EMI Limited, Hayes, England

[21] Appl. No.: 796,141

[22] Filed: May 12, 1977

[51] Int. Cl.² .............................................. G03B 41/16
[52] U.S. Cl. .................................................. 250/491
[58] Field of Search ............................ 250/491, 492 R

[56] References Cited

U.S. PATENT DOCUMENTS

| 2,659,824 | 11/1953 | Burnham | 250/491 |
| 2,887,586 | 5/1959 | Reininger | 250/491 |
| 3,082,322 | 3/1963 | Koerner | 250/523 |

Primary Examiner—Craig E. Church
Attorney, Agent, or Firm—Cooper, Dunham, Clark, Griffin & Moran

[57] ABSTRACT

A therapeutic radiographic apparatus includes a source of a pencil-like beam of penetrating radiation which requires to be positioned relative to a patient's body so that the radiation passes, at all times during therapy, through an anomaly, such as a tumor, in the patient's body. It is difficult to maintain coincidence of the beam with the anomaly, and this invention provides means for indicating optically a point of contact of the beam with the patient's body. The point of contact may, for example, be the point of emergence of the beam from the body.

6 Claims, 3 Drawing Figures

OPTICAL POINTER FOR RADIOGRAPHIC APPARATUS

The present invention relates to an optical alignment indicator for indicating the position of a beam of penetrating radiation, used in radiotherapy.

Therapeutic radiographic apparatus, for example x-ray apparatus, generally directs a relatively narrow beam of penetrating radiation through a patient disposed in the apparatus so that the beam intersects a feature, such as a tumour, to be irradiated.

Clearly, however, the beam of radiation cannot be seen by an operator and neither can the tumour unless it is surface feature. It is possible to prepare a patient for radiotherapy by determining the position of the tumour, for example by the use of computerised axial tomography (CAT) apparatus. The patient can then be marked, either directly or via an intermediate frame of reference, to indicate a desired path or paths for the radiation through the body. For proper use of such marking it is desirable to provide an indicator which marks the entrance of the radiation field at the patients body and also an indicator which marks the exit of the radiation field. If these two can be properly aligned the entire path of the radiation is effectively known. Means are known for projecting cross-hair shadows in a light beam onto a patient. To properly indicate the exit of the radiation field such projections are, however, placed opposite the radiation source on the centreline of and in the path of the radiation.

It is an object of this invention to provide a therapeutic radiographic apparatus including means disposed out of a path for the radiation beam of the apparatus defining optically that path to indicate a contact of the beam with the body, for example its exit therefrom.

It is another object of the invention to provide a therapeutic radiographic apparatus including a source arranged to provide a beam of penetrating radiation, at least two light sources each arranged to provide a planar divergent beam of light so that the at least two light beams intersect at a line substantially coincident with the central axis of path of the radiation beam.

It is another object of the invention to provide a therapeutic radiographic apparatus including means for supporting a patient in a desired position, a positioning structure, source means, mounted on the positioning structure for generating a beam of penetrating radiation and projecting the beam along a predetermined path to intersect the said position, means for moving the scanning structure, and with it the source means, to direct the radiation beam along different paths through said position and at least two light sources, mounted on the positioning structure, each light source arranged to provide a planar divergent beam of light so that the at least two light beams intersect in a line substantially coincident with central axis of said radiation beam.

Preferably the source means and light sources are disposed so that the light beams project at the said position, in a direction opposite to that of said radiation beam.

It is known to use low intensity light beams from sources, such as laser sources, for marker purposes. Such beams can be projected through optical systems such as cylindrical lenses to provide planar divergent (or fan-shaped) beams of light which are incident as lines on objects to be marked. Examples of such planar light sources include the 'isoline' laser light sources produced, for apparatus including radiographic equipment, by Gammex Inc. of Milwaukee, Wisconsin. Sources of this kind are particularly useful for implementing the present invention.

In order that the invention should be clearly understood and readily carried into effect an example thereof will now be described with reference to the accompanying drawings, of which:

Figure 1:
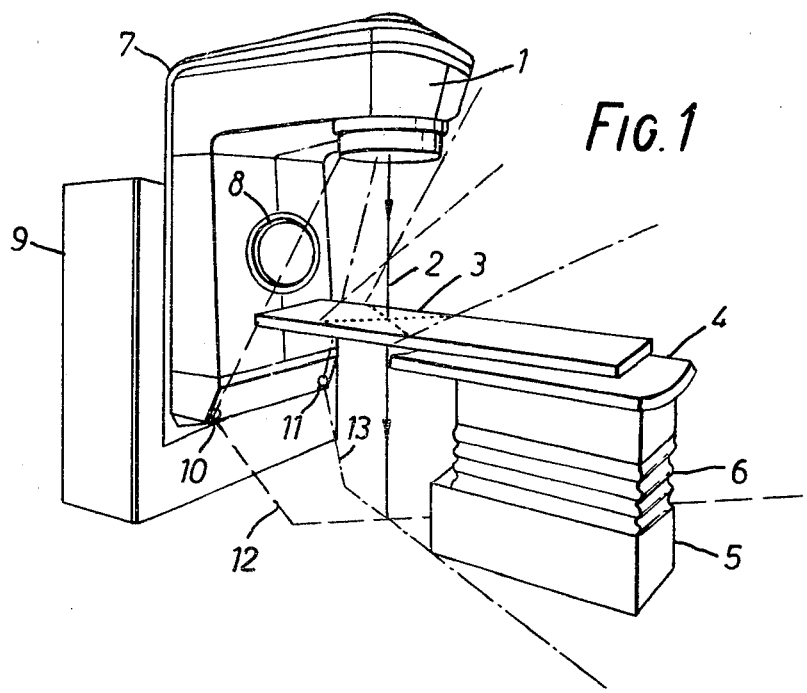
FIG. 1 shows in perspective view the general arrangement of the equipment.

Turning now to FIG. 1 there is shown an example of a therapeutic radiographic apparatus. A source, in this example an x-ray source, disposed in the equipment at 1, directs a beam 2 of radiation to intersect a couch 3 on which a patient can be supported. The radiation is indicated at 2 by the central axis of the radiation field. Couch 3 is supported on a base 4, and movable relative to that base by means not shown. A supporting pedestal 5 holds base 4 and includes a collapsible section 6 to allow vertical movement of base and couch by means also not shown.

The source 1 is mounted on a supporting and positioning structure 7 which is rotatably mounted at 8 on a floor mounted main structure 9. Structure 9 contains control equipment, power supplies and cooling fluid supplies which are carried into the positioning structure 7 as appropriate. Rotation of the positioning structure is about a horizontal axis intersecting the path of beam 2, through an angle which depends on the design of the equipment. The rotation in effect causes the radiation path to rotate about the point of intersection so that an object, such as a tumour, placed at that point is irradiated along a desired path.

Thus far the arrangement described is known for therapeutic radiographic apparatus. In this embodiment of the invention the positioning structure also carries two light sources 10 and 11. These may be lasers co-operating with cylindrical lenses and produce fan-shaped planar light beams 12, between limits of the broken lines, and 13, between the limits of the chain dotted lines, respectively.

Figure 2:
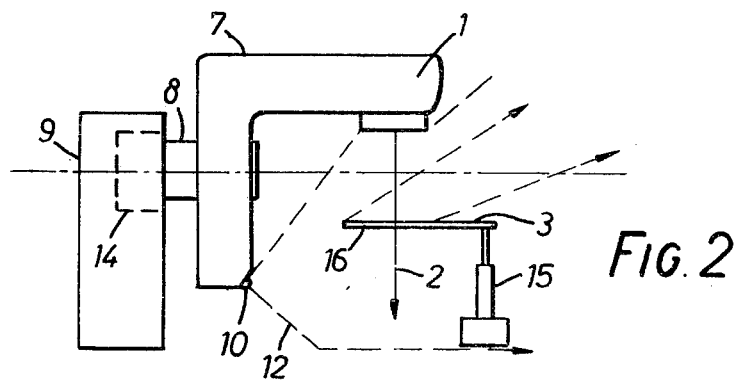
FIG. 2 shows a simplified side elevation of the equipment.
Figure 3:
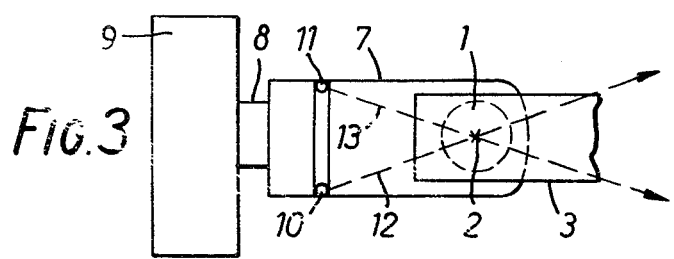
FIG. 3 shows a simplified plan of the equipment as viewed from beneath.

Beams 12 and 13 are arranged so that they intersect at a line which is substantially coincident with the central axis of the radiation (beam 2). The arrangement can also be seen in the side elevation and plan views of FIGS. 2 and 3, the latter being viewed from below. FIG. 2 also shows, in dotted outline, the drive means 14 used to rotate the positioning structure and a hydraulic ram 15 used to position the couch. The ram 15, which is usually hidden in the couch, could be more complex to provide additional movements.

It will be apparent that for the disposition of light sources shown, a patient disposed on couch 3 will be partially shielded from the light beams as at 16. However the beams project, on the underside of the couch, lines which intersect at the point of exit of the central axis of the radiation. If desired the sources 11 and 12, or additional sources, could be disposed at the upper part of the scanning structure to project lines which intersect at the point of entrance of the central axis. Normally the point of entrance is indicated by cross-hair shadows in a beam of light projected from the apparent radiation source.

In the course of rotation of the equipment on the positioning structure the illuminated exit point will trace a path about a patient on couch 3. If desired irradiation positions have been marked on the patient, or on a frame of reference fixed relative to the patient, then the patient can be moved by motion of couch 3 to correct for deviation of the illuminated point of exit from the desired positions.

What we claim is:

1. A therapeutic radiographic apparatus including a source arranged to provide a beam of penetrating radiation, at least two light sources each arranged to provide a planar divergent beam of light so that the at least two light beams intersect at a light substantially coincident with the central axis of the path of the radiation beam.

2. An apparatus according to claim 1 in which the light sources are disposed to project the planar beams of light substantially towards the source means to illuminate the exit of the radiation beam from an object disposed in the path of that beam.

3. A therapeutic radiographic apparatus including means for supporting a patient in a desired position, a positioning structure, source means, mounted on the positioning structure for generating a beam of penetrating radiation and projecting the radiation beam along a predetermined path to intersect the said position, means for moving the positioning structure, and with it the source means, to direct the radiation beam along different paths through said position and at least two light sources, mounted on the positioning structure, each light source arranged to provide a planar divergent beam of light so that the at least two light beams intersect in a line substantially coincident with the central axis of said radiation beam.

4. An apparatus according to claim 3 in which the light sources are disposed on the opposite side of said position from the source means to illuminate the exit point of the radiation beam from an object disposed in said position.

5. An apparatus according to claim 3 including means for moving the supporting means to align the patient in a desired relationship to the light beams and therefore with the radiation beam.

6. A method of maintaining a beam of radiation, directed from a therapeutic radiographic apparatus, through a patient, at a desired disposition in relation to said patient, including the steps of:
   (a) marking the desired point of exit or entrance of a central axis of the beam of radiation on the patient or a patient support,
   (b) directing two planar beams of light at the patient so that they intersect at a line substantially coincident with said central axis of the beam,
   (c) moving the patient support to align the projection of said line thereon with the marked point, and
   (d) directing a beam of the radiation through the patient along said central axis.

* * * * *

UNITED STATES PATENT AND TRADEMARK OFFICE
CERTIFICATE OF CORRECTION

PATENT NO. : 4,132,900
DATED : January 2, 1979
INVENTOR(S) : WILLIAM E. SMITH and ROBERT J. RORDEN It is certified that error appears in the above-identified patent and that said Letters Patent are hereby corrected as shown below:

Column 3, line 14 (Claim 1), "light" should read -- line --.

Signed and Sealed this

Eighth Day of July 1980

[SEAL]

Attest:

SIDNEY A. DIAMOND

Attesting Officer

Commissioner of Patents and Trademarks